(12) United States Patent
Lee et al.

(10) Patent No.: US 6,176,906 B1
(45) Date of Patent: Jan. 23, 2001

(54) QUATERNARY AMMONIUM SALT FOR PHOTO-CURABLE ANTIFOGGING COMPOSITION, METHOD FOR PREPARING THE SAME, AND PHOTO-CURABLE ANTIFOGGING COMPOSITION

(75) Inventors: Haeng-Woo Lee, Seoul; Young-Hoon Park; Sang-Keun Kim, both of Kyeongki-Do; Eun-A Shin, Seoul, all of (KR)

(73) Assignee: Ventree Co., Ltd. (KR)

( * ) Notice: Under 35 U.S.C. 154(b), the term of this patent shall be extended for 0 days.

(21) Appl. No.: 09/479,049

(22) Filed: Jan. 7, 2000

Related U.S. Application Data

(62) Division of application No. 09/088,784, filed on Jun. 1, 1998, now Pat. No. 6,096,925.

(30) Foreign Application Priority Data

Nov. 26, 1997 (KR) ................................... 97-62974

(51) Int. Cl.[7] ........................................ C09K 3/18
(52) U.S. Cl. ................... 106/13; 522/6; 522/8; 522/33; 522/121; 523/169; 524/186
(58) Field of Search ................ 106/13; 522/6, 522/8, 33, 121; 523/169; 524/186

(56) References Cited

U.S. PATENT DOCUMENTS 5,244,935 * 9/1993 Oshibe et al. ................... 522/151
5,262,475 * 11/1993 Creasy ................................ 525/58

FOREIGN PATENT DOCUMENTS 2-147639 * 6/1990 (JP).
3-177464 * 8/1991 (JP).
11-43614 * 2/1999 (JP).

* cited by examiner

Primary Examiner—Anthony Green
(74) Attorney, Agent, or Firm—Ostrolenk, Faber, Gerb & Soffen, LLP

(57) ABSTRACT

Disclosed is a photo-curable antifogging composition which may be applied to substrates such as glass, various plastic materials and the like to give antifogging property on the surface of these substrates. The main ingredient of the composition is a quaternary ammonium salt of the following formula (1):

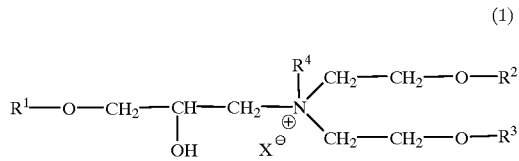

(1)

wherein:

$R^1$ is $CH_3(CH_2)_nCH_2$ or $CH_3(CH_2)_nCH_2C_6H_4$ wherein n is an integer from 1 to 16 inclusive;

$R^2$ and $R^3$ are the same or different from each other, and represent $CH_2=C(CH_3)COOCH_2CH(OH)CH_2$, $CH_2=CHCOOCH_2CH(OH)CH_2$ or H, with the proviso that $R^2$ and $R^3$ may not be H at the same time;

$R^4$ is H, $CH_3$, $CH_3CH_2$ or $CH_3CH_2CH_2$; and X is $CH_3OSO_3$, $CH_3CH_2OSO_3$, $CH_3COO$, $CF_3COO$, $CH_3(CH_2)_nCOO$ wherein n is an integer from 1 to 16 inclusive, $CH_3(CH_2)_7CH=CH(CH_2)_7COO$, $C_6H_5COO$, $C_6H_5CH(OH)COO$, $HOOCCH_2CH(OH)COO$, Cl or Br.

23 Claims, No Drawings

QUATERNARY AMMONIUM SALT FOR PHOTO-CURABLE ANTIFOGGING COMPOSITION, METHOD FOR PREPARING THE SAME, AND PHOTO-CURABLE ANTIFOGGING COMPOSITION

This is a division of application Ser. No. 09/088,784, filed Jun. 1, 1998 and now U.S. Pat. No. 6,096,925.

BACKGROUND OF THE INVENTION

1. Field of the Invention

The present invention relates to a quaternary ammonium salt which may be used for a photo-curable antifogging composition. More particularly, the present invention relates to a quaternary ammonium salt which may be used for the photo-curable antifogging composition which may be applied to the surface of substrates such as glass, various plastic materials and the like to provide antifogging properties on the surface of these substrates, a preparation method for the ammonium salt and the photo-curable antifogging composition including the same.

2. Description of the Prior Art

When articles such as swimming goggles, lenses, coverlets of measuring instruments, window glasses, various films and the like are placed in an environment in which a temperature difference between the internal and the external side is large, tiny water droplets are formed on the surface of these articles. In order to overcome this predicament, a method of applying an antifogging agent to a surface of an article has been suggested. Also, various research for a photo-curable antifogging composition that may be cured by UV irradiation has been conducted.

A conventional antifogging composition comprising hydrophilic substances such as polyvinylalcohol crosslinked with a catalyst such as peroxide is disclosed in U.S. Pat. No. 5,262,475. However, the processing temperature of the composition is about 150° C. Thus, it is difficult to apply the composition to a thin film due to the high processing temperature. Moreover, the crosslinked antifogging layer becomes sticky and then flows upon contact with water. The surface hardness of the layer is merely 6B as Pencil Hardness. Therefore, the layer may be scratched readily and thus cannot be used for a long time.

Another conventional antifogging method is to apply a solution of a surface active agent to a surface of a substrate. However, the substrate treated by such a method provides only a temporary antifogging property. An conventional antifogging method is to apply a polymeric surface active agent to a surface of the substrate in order to impart long-lasting antifogging property thereto.

Still another conventional method wherein a polymeric surface active agent is incorporated into a coating composition is also disclosed in Korean Patent Publication No. 95-14730. According to this method, however, a thermal drying process which should be continued for 20 to 180 seconds is needed to remove residual polar solvent from the antifogging composition. Moreover, UV irradiation which lasts for 20 to 60 seconds is required to cure the composition. Consequently, this method has a drawback of a low productivity caused by a two-step curing precess and a long treating time. Moreover, the antifogging property of the substrate treated by this method also reduces suddenly after 1 to 2 months.

To overcome the above described predicaments of the prior arts, the inventors of the present invention carried out extensive studies, and as a result found that antifogging compositions comprising a specific quaternary ammonium salt which contains photo-curable functional groups, and a photo-curable oligomer, provide good surface hardness, excellent adhesion properties, and excellent antifogging properties lasting a long time.

SUMMARY OF THE INVENTION

The first object of the present invention is therefore to provide a quaternary ammonium salt which may be employed as a principal ingredient of a composition which may form a cured film which has high surface hardness, excellent adhesion properties and excellent antifogging properties lasting a long time.

The second object of the present invention is to provide a preparation method for the quaternary ammonium salt.

The third object of the present invention is to provide a composition which may form a cured film which has high surface hardness, excellent adhesion properties and excellent antifogging properties lasting a long time.

The fourth object of the present invention is to provide a hybrid composition which may form a cured film which has high surface hardness, excellent adhesion properties and excellent antifogging properties lasting a long time.

In order to achieve the above first object, the present invention provides a quaternary ammonium salt of the following formula (1).

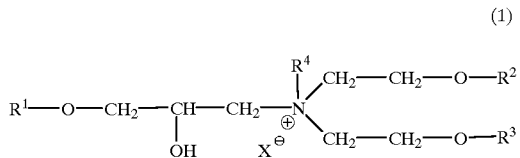

(1)

wherein:
$R^1$ is $CH_3(CH_2)_nCH_2$ or $CH_3(CH_2)_nCH_2C_6H_4$ wherein n is an integer from 1 to 16 inclusive;
$R^2$ and $R^3$ are the same or different from each other, and represent $CH_2=C(CH_3)COOCH_2CH(OH)CH_2$, $CH_2=CHCOOCH_2CH(OH)CH_2$ or H, with the proviso that $R^2$ and $R^3$ may not be H at the same time;
$R^4$ is H, $CH_3$, $CH_3CH_2$ or $CH_3CH_2CH_2$; and
X is $CH_3OSO_3$, $CH_3CH_2OSO_3$, $CH_3COO$, $CF_3COO$, $CH_3(CH_2)_nCOO$ wherein n is an integer from 1 to 16 inclusive, $CH_3(CH_2)_7CH=CH(CH_2)_7COO$, $C_6H_5COO$, $C_6H_5CH(OH)COO$, $HOOCCH_2CH(OH)COO$, Cl or Br.

In order to achieve the second object, the present invention also provides a method for preparing a quaternary ammonium salt of the above formula (1) which comprises the following steps (a) to (d):

(a) reacting alkyiglycidyl ether or alkylphenylglycidyl ether with protected di-2-hydroxyethylamine to give a compound of the following formula (2):

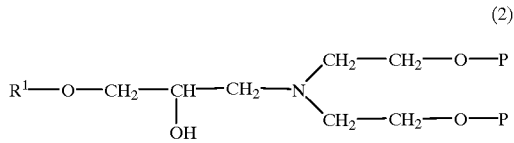

(2)

wherein:
$R^1$ is $CH_3(CH_2)_nCH_2$ or $CH_3(CH_2)_nCH_2C_6H_4$ wherein n is an integer from 1 to 16 inclusive; and P is an alcohol protecting group;
(b) deprotecting the compound of the above formula (2);
(c) reacting the deprotected compound with glycidyl acrylate or glycidyl methacrylate; and
(d) reacting the resulting tertiary amine with a compound of the formula $R^4X$ to give the quaternary ammonium salt.

In order to achieve the third object, the present invention also provides an antifogging composition which comprises the following ingredients (a) to (d):
(a) about 3-about 40% by weight of a quaternary ammonium salt of the above formula (1);
(b) about 18-about 90% by weight of an oligomer containing at least two acrylic groups;
(c) about 5-about 40% by weight of a first monomer containing at least one acrylic group; and
(d) about 2-about 8% by weight of a radical photoinitiator.

In order to achieve the fourth object, the present invention also provides a hybrid antifogging composition which comprises the following ingredients (a) to (f):
(a) about 3-about 34% by weight of a quaternary annnonium salt of the above formula (1);
(b) about 4-about 81% by weight of an oligomer containing at least two acrylic groups;
(c) about 6-about 26% by weight of a first monomer containing at least one acrylic group;
(d) about 8-about 26% by weight of a second monomer containing at least one vinyl ether group;
(e) about 1-about 5% by weight of a cationic photoinitiator; and
(f) about 1-about 5% by weight of a radical photoinitiator.

DETAILED DESCRIPTION OF THE INVENTION

Hereinafter, the present invention will be described in detail.

The photo-curable antifogging composition of the present invention essentially includes a quaternary ammonium salt of the following formula (1), which has one or two acryl groups, three hydroxy groups, one quaternary ammonium salt group, and one n-alkyl or n-alkylphenyl group:

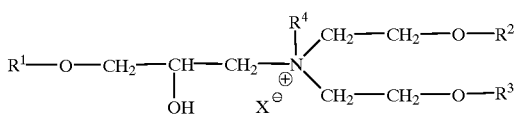

(1)

wherein:
$R^1$ is $CH_3(CH_2)_nCH_2$ or $CH_3(CH_2)_nCH_2C_6H_4$ wherein n is an integer from 1 to 16 inclusive;
$R^2$ and $R^3$ are the same or different from each other, and represent $CH_2$=$C(CH_3)COOCH_2CH(OH)CH_2$, $CH_2$=$CHCOOCH_2CH(OH)CH_2$ or H, with the proviso that $R^2$ and $R^3$ may not be H at the same time;
$R^4$ is H, $CH_3$, $CH_3CH_2$ or $CH_3CH_2CH_2$; and
X is $CH_3OSO_3$, $CH_3CH_2OSO_3$, $CH_3COO$, $CF_3COO$, $CH_3(CH_2)_nCOO$ wherein n is an integer from 1 to 16 inclusive, $CH_3(CH_2)_7CH$=$CH(CH_2)_7COO$, $C_6H_5COO$, $C_6H_5CH(OH)COO$, $HOOCCH_2CH(OH)COO$, Cl or Br.

The quaternary ammonium salt of the above formula (1) according to the present invention may be prepared by the following process.

Alkylglycidyl ether or alkylphenylglycidyl ether is reacted with protected di-2-hydroxyethylamine to give a compound of the following formula (2):

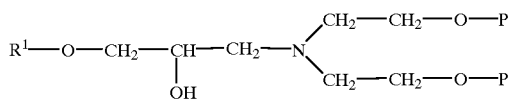

(2)

wherein:
$R^1$ is $CH_3(CH_2)_nCH_2$ or $CH_3(CH_2)_nCH_2C_6H_4$ wherein n is an integer from 1 to 16 inclusive; and
P is an alcohol protecting group.

The compound of the above formula (2) is deprotected to give an tertiary amine containing three hydroxy groups and one n-alkyl or n-alkylphenyl group. The resulting tertiary amine is converted into a quaternary ammonium salt by the reaction with a compound selected from the group of acetic acid, trifluoroacetic acid, benzoic acid, caprylic acid, mandelic acid, oleic acid, stearic acid, malic acid, dimethyl sulfate, diethyl sulfate, methyl chloride, ethyl chloride, propyl chloride, methyl bromide, ethyl bromide and propyl bromide.

The compound of the above formula (1) has a quaternary ammonium salt group, three hydroxy groups, one or two acrylic groups and a long chain alkyl group. The quaternary ammonium salt group and the hydroxy groups are hydrophilic and thus impart excellent antifogging property to a cured film prepared by a composition in which the compound of the above formula(1) is contained. The acrylic groups act as crosliking portions and thus enhance surface hardness of the cured film. The long chain alkyl group acts as a hydrophobic portion which helps to form a flat surface of the cured film and keeps the cured film from being weakened by excessive absorption of humidity.

The photo-curable antifogging composition according to the present invention includes about 3 to about 40% by weight of a compound of the above formula (1). If a content of the compound of the above formula (1) is less than about 3% by weight, the antifogging property of the cured film disappears. If the content of the compound of the above formula (1) exceeds about 40% by weight, the cured film is too brittle. Thus, the preferred content of the compound of the above formula (1) in the photo-curable antifogging composition according to the present invention is about 3-about 40% by weight, more preferably about 6-about 32% by weight.

The photo-curable antifogging composition includes (i) an oligomer containing at least two acryl groups. The oligomer which may be employed in the present invention is a compound such as urethane acrylate, epoxy acrylate, polyester acrylate or the like. These oligomers may be used solely or in a mixed form. If the content of the oligomer is less than about 18% by weight, adhesion of the cured film is very poor. If the content of the oligomer is more than about 90% by weight, viscosity of a composition is too large. Thus, the content of the oligomer in the antifogging composition is preferably about 18-about 90% by weight, and more preferably about 31-about 80% by weight.

The photo-curable antifogging composition also includes (ii) a first monomer containing at least one acryl group. The first monomer employed in the present invention is a compound such as isobornyl acrylate, hydroxyethyl acrylate, hydroxypropyl acrylate, hexanediol acrylate, tripropyleneglycol acrylate, triethylolpropyl triacrylate or the like.

If the content of the first monomer is less than about 5% by weight, viscosity of a composition is too large. If the content of the first monomer is more than about 40% by weight, adhesion of the cured film is very poor. Thus, the content of the first monomer is preferably about 5-about 40% by weight, and more preferably about 10-about 30% by weight.

The photo-curable antifogging composition also includes (iii) a radical photo-initiator. The radical photo-initiator which may be employed in the present invention is a compound such as 1-hydroxycyclohexyl phenyl ketone, 1-hydroxymethylethyl phenyl ketone or the like. If the content of the radical photo-initiator is less than about 2% by weight, it is difficult to initiate curing reaction. If the content of the radical photo-initiator is more than about 8% by weight, the storage stability of a composition is too low. Thus, the content of the radical photo-initiator is preferably about 2-about 8% by weight, and more preferably about 4about 7% by weight.

A hybrid photo-curable antifogging composition according to the present invention includes a compound of the above formula (1). If a content of the compound of the above formula (1) is less than about 3% by weight, the antifogging property of the cured film disappears. If the content of the compound of the above formula (1) exceeds about 34% by weight, the cured film is too brittle. Thus, the content of the compound of the above formula (1) in the photo-curable antifogging composition according to the present invention is preferably about 3-about 34% by weight, and more preferably about 4-about 32% by weight.

The hybrid photo-curable antifogging composition includes (i) an oligomer containing at least two acryl groups, as mentioned above. If the content of the oligomer is less than about 4% by weight, adhesion of the cured film is very poor. If the content of the oligomer is more than about 81% by weight, viscosity of a composition is too large. Thus, the content of the oligomer in the antifogging composition is preferably about 4-about 81% by weight, and more preferably about 10-about 74% by weight.

The hybrid photo-curable antifogging composition also includes (ii) a first monomer containing at least one acryl group, as mentioned above. If the content of the first monomer is less than about 6% by weight, viscosity of a composition is too large. If the content of the first monomer is more than about 26% by weight, adhesion of the cured film is very poor. Thus, the content of the first monomer is preferably about 6-about 26% by weight, and more preferably about 8-about 25% by weight.

The hybrid photo-curable antifogging composition also includes (iii) a radical photo-initiator, as mentioned above. If the content of the radical photo-initiator is less than about 1% by weight, it is difficult to initiate curing reaction. If the content of the radical photo-initiator is more than about 5% by weight, the storage stability of a composition is too low. Thus, the content of the radical photo-initiator is about 1-about 5% by weight, and more preferably about 2-about 4% by weight.

A hybrid photo-curable antifogging composition includes (iv) a second monomer containing at least one vinyl ether. The second monomer which may be employed in the present invention is, for example, triethyleneglycol divinyl ether. If the content of the second monomer is less than about 8% by weight, the surface hardness of a cured film is too low. If the content of the second monomer is more than about 26% by weight, the cured film becomes too sensitive to moisture. Thus, the content of the second monomer is preferably about 8-about 26% by weight, and more preferably about 10-about 25% by weight.

A hybrid photo-curable antifogging composition according to the present invention includes (v) a cationic photo-initiator. The cationic photo-initiator which may be employed in the present invention is a compound such as bis(4-diphenylsulfoniophenyl)sulfido bishexafluorophosphoric acid or the like. If the content of the cationic photo-initiator is less than about 1% by weight, the surface hardness of the cured film is too low. If the content of the cationic photo-initiator is more than about 5% by weight, the discoloration of the cured film happens. Thus, the content of the cationic photo-initiator is about 1-about 5% by weight, and more preferably about 2-about 4% by weight.

A cured film which has high surface hardness and excellent antifogging properties may be prepared using a composition wherein the compound of the above formula (1) is added to a conventional photo-curable coating agent (a mixture of (i), (ii) and (iii)). In addition, a cured film which has higher surface hardness and more excellent antifogging properties may be prepared using a composition wherein the compound of the above formula (1) is added to a hybrid photo-curable coating agent (a mixture of (i), (ii), (iii), (iv) and (v)) containing both a cationic photo-initiator and a radical photo-initiator).

The invention may be explained more specifically in connection with the following examples. However, the scope of the present invention is not to be limited thereby.

SYNTHETIC EXAMPLE 1

Preparation of [N-{2-(2-hydroxy-3-methacryloyloxy)propoxy}ethyl, N-(2-hydroxy- 3-dodecyloxy)propyl, N-(2-hydroxy)ethyl, N-methyl] ammonium methyl sulfate Dodecyl glycidyl ether (20.0 g) was poured into a three-neck flask, and the temperature of the content was raised to 50° C. Di-t-butyldimethylsilyloxyethylamine (18.2 g) was added dropwise into the flask. And then, the temperature of the content was kept below 55° C. After the addition was finished, the content was stirred at 55° C. for 3 hours. Then, the temperature of the content was lowered to 5° C. using an ice bath, and pyridinium hydrofluoride (14.2 g) was added using a syringe. And then, the temperature of the content was kept below 10° C. After the addition was finished, the content was stirred at 5° C. for 4 hours. Then, water and ethyl acetate were added, and an organic layer was separated and distilled to give a wanted intermediate. Then, the temperature of the intermediate was raised to 90° C., and glycidyl methacrylate (11.1 g) was added slowly. At this time, the temperature of the content was kept below 100° C. After the addition was finished, the content was stirred at 90° C. for 2 hours. Then, the temperature of the content was lowered to 40° C. using an ice bath, and dimethyl sulfate (8.7 g) was added dropwise. At this time, the temperature of the content was kept below 45° C. After the addition was finished, the content was stirred for 2 hours. By this method, the product of the present synthetic example was prepared.

Data of nuclear magnetic resonance (NMR) and a viscosity of the above product are as follows.

1H NMR (CDCl$_3$): 0.89 (m), 1.25 (m), 1.94 (m), 3.18 (m), 3.60 (m), 3.71 (s), 4.10 (m), 5.68 (m), 6.14 (m).

Viscosity (Brookfield viscometer): 500 cps (30° C.).

SYNTHETIC EXAMPLE 2

Preparation of [N,N-bis-[{2-(2-hydroxy-3-methacryloyloxy)propoxyl}ethyl], N-(2-hydroxy- 3-dodecyloxy)propyl, N-methyl]ammonium methyl sulfate Dodecyl glycidyl ether (20.0 g) was poured into a three-neck flask, and the temperature of the content was raised to 50° C. Di-t-butyldimethylsilyloxyethylamine (18.2 g) was added dropwise into the flask. At this time, the temperature of the content was kept below 55 ° C. After the addition was finished, the content was stirred at 55° C. for 3 hours. Then, the temperature of the content was lowered to 5° C. using an ice bath, and pyridinium hydrofluoride (14.2 g) was added using a syringe. At this time, the temperature of the content was kept below 10° C. After the addition was finished, the content was stirred at 5° C. for 2 hours. Then, water and ethyl acetate were added, and an organic layer was separated and distilled to give a wanted intermediate. Then, the temperature of the intermediate was raised to 90° C., and glycidyl methacrylate (23.5 g) was added slowly. At this time, the temperature of the content was kept below 95° C. After the addition was finished, the content was stirred at 95° C. for 2 hours. Then, the temperature of the content was lowered to 40° C. using an ice bath, and dimethyl sulfate (8.7 g) was added dropwise. At this time, the temperature of the content was kept below 45 ° C. After the addition was finished, the content was stirred for 2 hours. By this method, the product of the present synthetic example was prepared.

Data of nuclear magnetic resonance (NMR) and a viscosity of the above product are as follows.

1H NMR (CDCl$_3$) : 0.87 (m), 1.24 (m), 1.97 (m), 3.19 (m), 3.60 (m), 3.71 (s), 4.11 (m), 5.61 (m), 5.67 (m), 6.14 (m), 6.18 (m).

Viscosity (Brookfield viscometer): 430 cps (30° C.).

SYNTHETIC EXAMPLE 3

Preparation of [N-{2-(2-hydroxy-3-methacryloyloxy)propoxy}ethyl, N-(2-hydroxy-3-dodecyloxy)propyl, N-(2-hydroxy)ethyl]ammonium stearate Dodecyl glycidyl ether (20.0 g) was poured into a three-neck flask, and the temperature of the content was raised to 50° C. Di-t-butyldimethylsilyloxyethylamine (18.2 g) was added dropwise into the flask. At this time, the temperature of the content was kept below 55° C. After the addition was finished, the content was stirred at 55° C. for 3 hours. Then, the temperature of the content was lowered to 5° C. using an ice bath, and pyridinium hydrofluoride (14.2 g) was added using a syringe. At this time, the temperature of the content was kept below 10° C. After the addition was finished, the content was stirred at 5° C. for 2 hours. Then, water and ethyl acetate were added, and an organic layer was separated and distilled to give a wanted intermediate. After the temperature of the intermediate was raised to 90° C., glycidyl methacrylate (11.1 g) was added slowly. At this time, the temperature of the content was kept below 100° C. After the addition was finished, the content was stirred at 90° C. for 2 hours. Then, the temperature of the content was lowered to 40° C. using an ice bath, and stearic acid (23.6 g) was added dropwise. At this time, the temperature of the content was kept below 40 ° C. After the addition was finished, the content was stirred for 3 hours. By this method, the product of the present synthetic example was prepared.

Data of nuclear magnetic resonance (NMR) and a viscosity of the above product are as follows.

1H NMR (CDCl$_3$): 0.89 (m), 1.21–1.37 (m), 1.94–2.04 (m), 3.18 (m), 3.60 (m), 4.10 (m), 5.68 (m), 6.14 (m).

Viscosity (Brookfield viscometer): 520 cps (30 ° C.).

SYNTHETIC EXAMPLE 4

Preparation of [N,N-bis-[{2-(2-hydroxy-3-methacryloyloxy)propoxy}ethyl], N-(2-hydroxy-3-dodecyloxy)propyl]ammonium stearate Dodecyl glycidyl ether (20.0 g) was poured into a three-neck flask, and the temperature of the content was raised to 50° C. Di-t-butyldimethylsilyloxyethylamine (18.2 g) was added dropwise into the flask. At this time, the temperature of the content was kept below 55° C. After the addition was finished, the content was stirred at 55° C. for 3 hours. Then, the temperature of the content was lowered to 5° C. using an ice bath, and 14.2 g of pyridinium hydrofluoride was added using a syringe. At this time, the temperature of the content was kept below 10° C. After the addition was finished, the content was stirred at 5° C. for 2 hours. Then, water and ethyl acetate were added, and an organic layer was separated and distilled to give a wanted intermediate. After the temperature of the intermediate was raised to 90° C., glycidyl methacrylate (23.5 g) was added slowly. At this time, the temperature of the content was kept below 95° C. After the addition was finished, the content was stirred at 90° C. for 2 hours. Then, the temperature of the content was lowered to 40° C. using an ice bath, and stearic acid (23.6 g) was added dropwise. At this time, the temperature of the content was kept below 45° C. After the addition was finished, the content was stirred for 3 hours. By this method, the product of the present synthetic example was prepared.

Data of nuclear magnetic resonance (NMR) and a viscosity of the above product are as follows.

1H NMR (CDCl$_3$): 0.87–0.91 (m), 1.21–1.35 (m), 1.97 (m), 3.19 (m), 3.60 (m), 4.21 (m), 4.72 (m), 5.57 (m) 6.20 (m), 6.27 (m).

Viscosity (Brookfield viscometer): 440 cps (30° C.).

SYNTHETIC COMPARATIVE EXAMPLE 1

Preparation of {N-(2-methacryloyloxy)ethyl, N,N-dimethyl}ammonium trifluoroacetic acid Dimethylaminoethyl methacrylate (157 g (1 mole)) was added into a three-neck flask equipped with a thermometer, a reflux condenser, an adding funnel, a magnetic spin bar and a magnetic stirrer, and then the content was cooled using an ice bath. After the content was cooled below 10° C., trifluoroacetic acid (114 g (1 mole)) was added dropwise using an addition funnel, the reaction temperature being below 30° C. After the addition was finished, the reaction mixture was stirred for 1 hour. By this method, the product of the present synthetic comparative example was prepared.

Data of nuclear magnetic resonance (NMR) and a viscosity of the above product are as follows.

1H NMR (CDCl$_3$): 0.87 (m), 1.24 (m), 1.97 (m), 3.19 (m), 3.60 (m), 3.71 (s), 4.11 (m), 4.67 (m), 5.61 (m) 6.14 (m), 6.18 (m).

Viscosity (Brookfield viscometer): 200 cps (30° C.).

Antifogging compositions were prepared using the compounds of the above synthetic examples 1–4 or synthetic comparative example 1, and other ingredients according to mixing ratios of the following table 1.

EXAMPLE 1

40% by weight of urethane acrylate (CN985B88™ of Sartomer); 4% by weight of tripropyleneglycol diacrylate (SR306™ of Sartomer); 5% by weight of trimethylolpropane triacrylate (SR351™ of Sartomer); 3% by weight of 1-hydroxycyclohexyl phenyl ketone (IRG-184™ of Sartomer); 3% by weight of bis(4-diphenylsulfoniophenyl) sulfido bishexafluorophosphoric acid (CD1011™ of Sartomer); 15% by weight of triethyleneglycol divinyl ether (DVE-3™ of ISP); and 30% by weight of a compound of synthetic example 1 were mixed to give an antifogging composition. Table 1 represents mixing ratios.

EXAMPLES 2–12

An antifogging composition was prepared using ingredients of table 1 according to the same method as that of the above Example 1.

Comparative Examples 1–3

An antifogging composition was prepared using ingredients of table 1 according to the same method as that of the above Example 1.

A polyester film was coated so that a thickness of a dried film formed thereon may be 5 μm, then the coated polyester film passed through a UV lamp (300 mJ/cm$^2$) once. The resulting cured film was cross-cut. After cellophane tape was attached and detached a hundred times, a number of remaining parts was counted. The number is disclosed in the following table 2.

Antifogging Property

After a cured film was formed on a transparent glass plate according to KS M 2472, water vapor was blown on a cured film intermittently by a water vapor generator, until cloudi-

TABLE 1 unit: % by weight

|  | ex. 1 | ex. 2 | ex. 3 | ex. 4 | ex. 5 | ex. 6 | ex. 7 | ex. 8 | ex. 9 | ex. 10 | ex. 11 | ex. 12 | com. 1 | com. 2 | com. 3 |
|---|---|---|---|---|---|---|---|---|---|---|---|---|---|---|---|
| urethane acrylate | 40 | 50 | 40 | 50 | 40 | 50 | 40 | 50 | 40 | 40 | 50 | 60 | 40 | 40 | 50 |
| TPGDA | 4 | 11 | 4 | 11 | 4 | 11 | 4 | 11 | 6 | 18 | 11 | 21 | 9 | 4 | 9 |
| TMPTA | 5 | 5 | 5 | 5 | 5 | 5 | 5 | 5 | 5 | 5 | 5 | 5 | 5 | 5 | 5 |
| IRGACURE-184 | 3 | 3 | 3 | 3 | 3 | 3 | 3 | 3 | 3 | 3 | 6 | 6 | 2 | 2 | 6 |
| CD1011 | 3 | 3 | 3 | 3 | 3 | 3 | 3 | 3 | 3 | 3 |  |  | 4 | 4 |  |
| DVE-3 | 15 | 23 | 15 | 23 | 15 | 23 | 15 | 23 | 15 | 23 |  |  | 40 | 15 |  |
| cpd. of s. ex. 1 | 30 | 5 |  |  |  |  |  |  | 7 | 2 | 7 | 2 |  |  |  |
| cpd. of s. ex. 2 |  |  | 30 | 5 |  |  |  |  | 7 | 2 | 7 | 2 |  |  |  |
| cpd. of s. ex. 3 |  |  |  |  | 30 | 5 |  |  | 7 | 2 | 7 | 2 |  |  |  |
| cpd. of s. ex. 4 |  |  |  |  |  |  | 30 | 5 | 7 | 2 | 7 | 2 |  |  |  |
| cpd of s. com. 1 |  |  |  |  |  |  |  |  |  |  |  |  |  | 30 | 30 |
| sum | 100 | 100 | 100 | 100 | 100 | 100 | 100 | 100 | 100 | 100 | 100 | 100 | 100 | 100 | 100 | wherein:
- ex., com., cpd., s.ex., and s.com. are respectively abbreviations of example, comparative example, compound, synthetic example, and synthetic comparative example;
- urethane acrylate is CN985B88™ of Sartomer;
- TPGDA (tripropyleneglycol diacrylate) is SR306™ of Sartomer;
- TMPTA (trimethylolpropane triacrylate) is SR351™ of Sartomer; and
- IRGACURE-184 (1-hydroxycyclohexyl phenyl ketone) is IRG-184™ of Sartomer;
- CD1011 (bis(4-diphenylsulfoniophenyl)sulfido bishexafluorophosphoric acid) is CD1011™ of Sartomer; and
- DVE-3 (triethyleneglycol divinyl ether) is DVE-3™ of ISP.

ness or dew was formed, and a number of times water vapor was blown on the cured film was counted. The number is disclosed in table 2.

Pencil Hardness

Pencil hardness was estimated by the following inspection according to ASTM D3363-92a. "UNI" pencils (Mitsubishi pencil manufactured by K. K.) of 17 kinds were used for the tests. The pencil hardness has 17 levels of 9H–1H, F, HB, and 1B–6B. Each pencil was attached to a scratching test instrument, and the hardness of cured films were estimated. A weight of 1 kg was loaded on each pencil, and then each loaded pencil was moved on the cured film in a velocity of 0.5 mm/s.

Results of the tests for cured films are as follows.

TABLE 2

|  | ex. 1 | ex. 2 | ex. 3 | ex. 4 | ex. 5 | ex. 6 | ex. 7 | ex. 8 | ex. 9 | ex. 10 | ex. 11 | ex. 12 | com. 1 | com. 2 | com. 3 |
|---|---|---|---|---|---|---|---|---|---|---|---|---|---|---|---|
| Cure extent | G | VG | VG | VG | G | VG | VG | VG | VG | VG | G | G | VG | G | F |
| adhesion | 100 | 100 | 100 | 100 | 100 | 100 | 100 | 100 | 100 | 100 | 100 | 100 | 100 | 90 | 80 |
| antifogging property | ≧20 | ≧20 | ≧20 | ≧20 | ≧20 | ≧20 | ≧20 | ≧20 | ≧20 | ≧20 | ≧20 | ≧20 | 0 | 2 | 5 |
| pencil hardness | 1H | 4H | 2H | 4H | 1H | 4H | 2H | 4H | 2H | 3H | 1H | 2H | 1B | 2B | 3B |

Preparation of Test Pieces

Glass plates or polyester films were coated with compositions of the examples 1–12 and comparative examples 1–3, then the coated substrates passed through an UV drier to give cured films.

Test of Test Pieces

Cure Extent

A glass plate was coated so that a thickness of a dried film formed thereon may be 5 μm, then the coated glass plate passed through a UV lamp (300 mJ/cm$^2$) once. Then, a state of a cured film was estimated.

Adhesion: ASTM D3359-92a wherein:
- ex. and com. are respectively abbreviations of example and comparative example.

In estimating cure extent, VG means no stickiness of surface, and no damage on a cured film when it is rubbed 100 times using methyl ethyl ketone. G means no stickiness of surface and some damages on a cured film when it is rubbed 50 times using methyl ethyl ketone. F means no stickiness of surface and some damages in a cured film when it is rubbed 10 times using methyl ethyl ketone.

As you may guess from table 2, cured film formed using composition according to each of examples 1–12 has very excellent antifogging properties (passing more than 20 times) and very excellent surface hardness (pencil hardness is 1–4H). However, cured film formed using composition according to example 1, 5, 11 or 12 has a somewhat inferior cure extent. Cured film formed using composition according to comparative example 1 has no antifogging property and has inferior surface hardness (a pencil hardness is 1B). Cured film formed using composition according to comparative example 2 or 3 has little antifogging property (passing more than 2–5 times) and has inferior surface hardness (a pencil hardness is 2B–3B).

Cured films formed using compositions according to the present invention have high surface hardness, excellent adhesion properties and excellent antifogging properties lasting a long time.

What is claimed is:

1. An antifogging composition comprising the following ingredients (a), (b), (c) and (d):
   (a) about 3-about 40% by weight of a quaternary ammonium salt of the following formula (1):

$$R^1-O-CH_2-CH(OH)-CH_2-\overset{\oplus}{N}(R^4)(CH_2-CH_2-O-R^2)(CH_2-CH_2-O-R^3) \cdot X^\ominus \quad (1)$$

wherein:
   $R^1$ is $CH_3(CH_2)_nCH_2$ or $CH_3(CH_2)_nCH_2C_6H_4$ wherein n is an integer from 1 to 16 inclusive;
   $R^2$ and $R^3$ are the same or different from each other, and represent $CH_2=C(CH_3)COOCH_2CH(OH)CH_2$, $CH_2=CHCOOCH_2CH(OH)CH_2$ or H, with the proviso that $R^2$ and $R^3$ may not be H at the same time;
   $R^4$ is H, $CH_3$, $CH_3CH_2$ or $CH_3CH_2CH_2$; and
   X is $CH_3OSO_3$, $CH_3CH_2OSO_3$, $CH_3COO$, $CF_3COO$, $CH_3(CH_2)_nCOO$ wherein n is an integer from 1 to 16 inclusive, $CH_3(CH_2)_7CH=CH(CH_2)_7COO$, $C_6H_5COO$, $C_6H_5CH(OH)COO$, $HOOCCH_2CH(OH)COO$, Cl or Br;
   (b) about 18-about 90% by weight of an oligomer containing at least two acrylic groups;
   (c) about 5-about 40% by weight of a monomer containing at least one acrylic group; and
   (d) about 2-about 8% by weight of a radical photo-initiator.

2. An antifogging composition according to claim 1, wherein the oligomer is selected from the group consisting of urethane acrylate, epoxy acrylate and polyester acrylate.

3. An antifogging composition according to claim 1, wherein the monomer is selected from the group consisting of isobonyl acrylate, hydroxyethyl acrylate, hydroxypropyl acrylate, hexanediol acrylate, tripropyleneglycol acrylate and triethylolpropyl triacrylate.

4. An antifogging composition according to claim 1, wherein the radical photo-initiator is selected from the group consisting of 1-hydroxycyclohexyl phenyl ketone and 1-hydroxymethylethyl phenyl ketone.

5. An antifogging composition according to claim 1 wherein the amount of (a) is about 6-about 32%, the amount of (b) is about 31-about 80%, the amount of (c) is about 10-about 30%, and the amount of (d) is about 4-about 7%.

6. An antifogging composition according to claim 5 wherein the oligomer is selected from the group consisting of urethane acrylate, epoxy acrylate and polyester and the first monomer is selected from the group consisting of iosbonyl acrylate, hydroxyethyl acrylate, hydroxypropyl acrylate, hexanediol acrylate, tripropyleneglycol acrylate and triethylolpropyl triacrylate and wherein the radical photoinitiator is selected from the group consisting of 1-hydroxycyclohexyl phenyl ketone and 1-hydroxymethylethyl phenyl ketone.

7. An antifogging composition according to claim 1 wherein in the quaternary ammonium salt, $R^1$ is dodecyl, $R^2$ is $CH_2=CH(CH_3)COOCH_2CH(OH)CH_2$, $R^3$ is $CH_2=CH(CH_3)COOCH_2CH(OH)CH_2$ or hydrogen and $R^4$ is H or $CH_3$.

8. An antifogging composition according to claim 1 wherein X is methane sulfate or stearate.

9. An antifogging composition according to claim 1 in which (a) is [N-{2-(2-hydroxy-3-methacryloyloxy)propoxy}ethyl, N-(2-hydroxy-3-dodecyloxy)propyl, N-(2-hydroxy)ethyl, N-methyl]ammonium methyl sulfate.

10. An antifogging composition according to claim 1 in which (a) is [N,N-bis-[{2-(2-hydroxy-3-methacryloyloxy)propoxy}ethyl], N-(2-hydroxy-3-dodecyloxy)propyl, N-methyl]ammonium methyl sulfate.

11. An antifogging composition according to claim 1 in which (a) is [N-{2-(2-hydroxy-3-methacryloyloxy)propoxy}ethyl, N-(2-hydroxy-3-dodecyloxy)propyl, N-(2-hydroxy)ethyl]ammonium stearate.

12. An antifogging composition according to claim 1 in which (a) is [N,N-bis-[{2-(2-hydroxy-3-methacryloyloxy)propoxy}ethyl], N-(2-hydroxy-3-dodecyloxy)propyl] ammonium stearate.

13. A hybrid antifogging composition comprising the following ingredients (a) to (f):
   (a) about 3-about 34% by weight of a quaternary ammonium salt of the following formula (1):

$$R^1-O-CH_2-CH(OH)-CH_2-\overset{\oplus}{N}(R^4)(CH_2-CH_2-O-R^2)(CH_2-CH_2-O-R^3) \cdot X^\ominus \quad (1)$$

wherein:
   $R^1$ is $CH_3(CH_2)_nCH_2$ or $CH_3(CH_2)_nCH_2C_6H_4$ wherein n is an integer from 1 to 16 inclusive;
   $R^2$ and $R^3$ are the same or different from each other, and represent $CH_2=C(CH_3)COOCH_2CH(OH)CH_2$, $CH_2=CHCOOCH_2CH(OH)CH_2$ or H, with the proviso that $R^2$ and $R^3$ may not be H at the same time;
   $R^4$ is H, $CH_3$, $CH_3CH_2$ or $CH_3CH_2CH_2$; and
   X is $CH_3OSO_3$, $CH_3CH_2OSO_3$, $CH_3COO$, $CF_3COO$, $CH_3(CH_2)_nCOO$ wherein n is an integer from 1 to 16 inclusive, $CH_3(CH_2)_7CH=CH(CH_2)_7COO$, $C_6H_5COO$, $C_6H_5CH(OH)COO$, $HOOCCH_2CH(OH)COO$, Cl or Br;
   (b) about 4-about 81% by weight of an oligomer containing at least two acrylic groups;
   (c) about 6-about 26% by weight of a first monomer containing at least one acrylic group;
   (d) about 8-about 26% by weight of a second monomer containing at least one vinyl ether group;
   (e) about 1-about 5% by weight of a cationic photo-initiator; and
   (f) about 1-about 5% by weight of a radical photo-initiator.

14. A hybrid antifogging composition according to claim 13 wherein the second monomer is triethyleneglycol divinyl ether.

15. A hybrid antifogging composition according to claim 13 wherein the cationic photo-initiator is bis(4-diphenylsulfonophenyl)sulfodo bishexafluorophosphoric acid.

16. A hybrid antifogging composition according to claim 13 wherein the amount of (a) is about 4-about 32%, the amount of (b) is about 10-about 26%, the amount of (c) is about 8-about 25%, the amount of (d) is about 10-about 25%, the amount of (e) is about 2-about 4% and the amount of (f) is about 2-about 4%.

17. A hybrid antifogging composition according to claim 16 wherein the second monomer is triethyleneglycol divinyl ether and the cationic photo-initiator is bis(4-diphenylsulfonophenyl)sulfodo bishexafluorophosphoric acid.

18. A hybrid antifogging composition according to claim 13 wherein in the quaternary ammonium salt, $R^1$ is dodecyl, $R^2$ is $CH_2=CH(CH_3)COOCH_2CH(OH)CH_2$, $R^3$ is $CH_2=CH(CH_3)COOCH_2CH(OH)CH_2$ or hydrogen and $R^4$ is H or $CH_3$.

19. A hybrid antifogging composition according to claim 13 wherein X is methane sulfate or stearate.

20. A hybrid antifogging composition according to claim 13 in which (a) is [N-{2-(2-hydroxy-3-methacryloyloxy)propoxy}ethyl, N-(2-hydroxy-3-dodecyloxy)propyl, N-(2-hydroxy)ethyl, N-methyl]ammonium methyl sulfate.

21. A hybrid antifogging composition according to claim 13 in which (a) is [N,N-bis-[{2-(2-hydroxy-3-methacryloyloxy)propoxy}ethyl], N-(2-hydroxy-3-dodecyloxy)propyl, N-methyl]ammonium methyl sulfate.

22. A hybrid antifogging composition according to claim 13 in which (a) is [N-{2-(2-hydroxy-3-methacryloyloxy)propoxy}ethyl, N-(2-hydroxy-3-dodecyloxy)propyl, N-(2-hydroxy)ethyl]ammonium stearate.

23. A hybrid antifogging composition according to claim 13 in which (a) is [N,N-bis-[{2-(2-hydroxy-3-methacryloyloxy)propoxy}ethyl], N-(2-hydroxy-3-dodecyloxy)propyl]ammonium stearate.

* * * * *